US005650627A

United States Patent [19]
Reed et al.

[11] Patent Number: 5,650,627
[45] Date of Patent: Jul. 22, 1997

[54] SENSITIVE ASSAY METHOD FOR MEASURING GALLIUM LEVELS IN BODY TISSUES AND FLUIDS

[75] Inventors: Eddie Reed, Germantown; Kang Bo Lee, Gaithersburg, both of Md.

[73] Assignee: The United States of America as represented by the Department of Health and Human Services, Washington, D.C.

[21] Appl. No.: 355,153

[22] Filed: Dec. 8, 1994

[51] Int. Cl.⁶ ................................................ G01N 21/74
[52] U.S. Cl. ............................................. 250/372; 356/311
[58] Field of Search ................................. 250/372, 373; 356/307, 311

[56] References Cited

U.S. PATENT DOCUMENTS

| | | | |
|---|---|---|---|
| 5,106,189 | 4/1992 | Moriya et al. | 356/307 |
| 5,225,182 | 7/1993 | Sharma. | |
| 5,315,528 | 5/1994 | L'vov | 356/307 X |

FOREIGN PATENT DOCUMENTS

| | | | |
|---|---|---|---|
| 1-302141 | 12/1989 | Japan | 356/311 |
| 1216726 | 3/1986 | U.S.S.R. | 356/311 |

OTHER PUBLICATIONS

Cernik, "A Preliminary Procedure for the Determination of Cadmium in Blood," Atomic Absorption Newsletter, vol. 12, No. 6, 1973, pp. 163–164.

K. B. Lee, Proceedings of the American Association for Cancer Research, vol. 36, p. 312, 1857 (1995).
E. Reed et al., "Quantitation of Platinum–DNA Binding After Therapeutic Levels of Drug Exposure—A Novel Use of Graphite Furnace Spectrometry," Atomic Spectroscopy, May–Jun. 1988, vol. 9, No. 3, pp. 93–95.
D. P. Kelsen et al., "Pharmacokinetics of Gallium Nitrate in Man," Cancer, vol. 46, 1980, pp. 2009–2013.
S. W. Hall et al., "Kinetics of gallium nitrate, a new anticancer agent," Clin Pharmacol. Ther., vol. 25, No. 1, Jan. 1979, pp. 82–87.

Primary Examiner—Edward J. Glick
Attorney, Agent, or Firm—Birch, Stewart, Kolasch & Birch, LLP

[57] ABSTRACT

A sensitive assay method for measuring the quantity of elemental gallium present in a test sample comprising a body tissue or a body fluid, the method comprising:

- diluting a test sample with nitric acid,
- introducing the diluted test sample into an atomic absorption spectrometer having a Zeeman-effect background correction calculating capability,
- determining the test sample's absorption at a desired wavelength while subjecting the test sample to an atomization and a burning in the atomic absorption spectrometer,
- performing a Zeeman-effect background correction on the determined absorption for the test sample to give a corrected absorption for the test sample, and
- comparing the corrected absorption for the test sample with a standard curve.

6 Claims, No Drawings

SENSITIVE ASSAY METHOD FOR MEASURING GALLIUM LEVELS IN BODY TISSUES AND FLUIDS

FIELD OF THE INVENTION

A physical chemistry assay method using atomic absorption spectroscopy for the measurement of elemental gallium in quantities as small as about 25 picograms in bodily fluids and tissues of malignant and non-malignant origin.

BACKGROUND OF THE INVENTION

Pharmacokinetic studies have been reported in human patients, with disseminated neoplasms refractory to conventional chemotherapy, who received gallium nitrate at doses of 600 mg/m$^2$ intravenously in a phase I clinical trial; S. W. Hall, et al., *Clin. Parmacol. Ther.*, Vol. 25, No. 1, pp. 82–87 (1979). In these reported studies gallium levels in biological fluids were analyzed by a modification of the colorimetric techniques of Willard and Fogg (*J. Amer. Chem. Soc.*, Vol. 59, pp. 40–45 (1937)), which involved adding titanous chloride to the sample and extracting with isopropyl ether, and then allowing the isopropyl extract to react hydroxylamine hydrochloride and rhodamine B to obtain a colored gallium complex. The colored complex was extracted with toluene and absorbance at 565 nm was read with a spectrophotometer. It was reported that standard curves in plasma and urine were linear between concentrations of 1 and 60 micrograms/milliliter.

The pharmacokinetics of Gallium Nitrate in humans was also studied and reported by D. P. Kelsen, et al., *Cancer*, Vol. 46, pp. 2009–2013 (1980). Kelsen et al. assayed for gallium levels in plasma and urine by flameless atomic absorption spectrophotometry (AAS) using a PERKIN-ELMER 372 atomic absorption spectrophotometer. It was reported that gallium metal (500 mg) was dissolved in 5 ml of concentrated nitric acid and diluted with water to 1 liter, with standards being prepared daily by appropriate dilution. The working range was indicated to be 0.1–2.0 micrograms/ml for aqueous standards and 0.1–0.5 micrograms/ml, when 0.5N HNO$_3$ or plasma were used as diluents. It was reported that gallium levels as low as 0.025 micrograms/ml were measurable in plasma treated and in urine diluted with 0.5N HNO$_3$, and that sensitivity was decreased approximately five-fold in aqueous solutions of standards or urine.

Reed et al., *Atomic Spectroscopy*, Vol. 9, No. 3, pp. 93–95 (1988), reported that the ability to measure elemental platinum was enhanced by more than a log, using Atomic Absorption Spectroscopy methods with Zeeman background correction. In this respect, a series of tissue culture studies have been performed using cisplatin or carboplatin, using the method reported by Reed et al.

SUMMARY OF THE INVENTION

The present invention provides a highly sensitive assay method for measuring the level of elemental gallium present in body tissues and fluids. The assay method employs an atomic absorption spectrometer having Zeeman-effect background correction capabilities. By using the inventive assay method gallium levels can be measured in a test sample of body tissue or fluid to a sensitivity of about 25 picograms.

The inventive assay method more specifically allows one to sensitively measure the quantity of elemental gallium present in a test sample comprising a body tissue or a body fluid by carrying out the steps of:

diluting said test sample with nitric acid, introducing said diluted test sample into an atomic absorption spectrometer having a Zeeman-effect background correction calculating capability, determining said test sample's absorption at a desired wavelength while subjecting said test sample to an atomization and a burning in said atomic absorption spectrometer, performing a Zeeman-effect background correction on said determined absorption for said test sample to give a corrected absorption for said test sample, and comparing said corrected absorption for said test sample with a standard curve.

In the assay method said test sample's absorption is preferably determined at a wavelength of about 287 nanometers, more preferably about 287.4 nanometers.

Preferably, said test sample is diluted in a matrix of less than about 2% (volume/volume) of nitric acid, more preferably less than about 1% (volume/volume) of nitric acid, and most preferably contains about 0.2% (volume/volume) nitric acid.

Preferably, the body tissue or fluid test sample to be analyzed is that of a human, and preferably the test sample has a volume of about 50 microliters or less.

Since the present inventive assay method has a detection limit of about 25 picograms of elemental gallium, as compared to a calculated 0.5 micrograms (500 picograms) of gallium for the reported method of Kelsen et al., supra., this produces at least two notable advantages:

1. It allows for the measurement of gallium in tissue culture settings, after micromolar levels of drug use. This was not possible before the present invention. This opens the possibility for a number of molecular studies that were not possible with prior methods.

2. It allows for the measurement of "free" gallium in body fluids (blood, urine, etc.), as well as gallium binding to specific subcellular molecules in human tissues. This has not been possible using previous methods.

DETAILED DESCRIPTION OF THE INVENTION

The following detailed description is provided as an aid to those desiring to practice the present invention. The examples provided herein are not to be construed as limiting to the present inventive discovery, since those skilled in the art realize that changes and modifications can be made in the materials and procedures set forth herein without departing from the spirit or scope of the present inventive discovery.

The present inventive assay method depends in part to the use of an atomic absorption spectrometer (AAS) having the ability to perform a Zeeman-effect background correction calculation. Such spectrometers are well known in the art and are commercially available. For example, such a spectrometer was used by Reed et al. supra., in order to quantify platinum-DNA binding after therapeutic exposure to cisplatin. Exemplary of such a spectrometer is the PERKIN-ELMER 3030B, which was used in the Example provided below.

Whatever atomic absorption spectrometer is chosen to practice the inventive assay methods, it should have the capability to perform a Zeeman-effect background correction calculation, in order to fully enjoy the high degree of sensitivity that is possible with the inventive assay methods. Further, whatever atomic absorption spectrometer is chosen, it should be operated according to the manufacturers instructions, and in accordance with standard atomic absorption spectroscopy techniques utilized by those skilled in the art. In this respect, the following texts on atomic absorption spectroscopy and atomic absorption spectroscopy techniques are mentioned and are incorporated herein by reference, in their entirety:

Walter Slavin, *Graphite Furnace Technology and Atomic Absorption Spectroscopy*, Pergamon Press, Oxford and New York (1984);

P.W.J.M. Boumans, *Atomic Absorption Spectroscopy Past Present and Future*, Pergamon Press, Oxford and New York (1980 & 1981); and Asha Varma, *CRC Handbook of Atomic Absorption Analysis*, CRC Press, Boca Raton, Fla, USA (1994).

The present inventive assay methods are applicable to a variety of body tissues and fluids. For example they are applicable to plasma, urine, blood, etc., of both human and non-human origin. Moreover, because the present inventive methods are highly sensitive to the presence of gallium—they allow one to study the subcellular effects of gallium. As a result, it is possible to use the present assay methods to measure gallium levels in bacteria (e.g., *E. coli*), yeast, ground tissues and cell cultures, all of which are encompassed by the use of the terms "body tissues" and "body fluids," as they are used herein and in the accompanying claims.

EXAMPLE

Using a PERKIN-ELMER 3030B graphite furnace atomic absorption spectrometer (AAS), with Zeeman-effect Background correction, in order to measure gallium levels in biological fluids, instrumental conditions were set to a wavelength of 287.4 nanometers and 20W lamp current.

Sample sizes to be analyzed were 50 microliters, charting temperatures of 130° C., pretreatment at 800° C., atomization at 2400° C., and burn off at 2600° C.

Standard curves were made using multiple injections of a range of 0.5 to 40 nanograms/ml of elemental gallium in matrices of $dH_2O$ and 0.2% nitric acid ($HNO_3$).

Gallium could be measured in the range of 75 picograms to 10 nanograms for $dH_2O$ ($y=0.0121x+0.00241$ ($r=0.985$)) and 25 picograms to 6 nanograms for 0.2% $HNO_3$ ($y=0.0468x+0.0077$ ($r=0.988$)).

To determine gallium recovery, 10–70 nanograms of elemental gallium were spiked into untreated PC3 cells and gallium levels were measured by AAS. The highest and lowest recovery was 84.9% and 67.2% in samples spiked with 10 nanograms and 70 nanograms respectively. The overall recovery rate was 78.0±8.0%.

The present inventive assay method with using a 0.2% (volume/volume) $HNO_3$ matrix for analysis of gallium permitted the determination of low levels of gallium with very good reproducibility in biological materials.

Each of the publications and patent documents referred to herein are incorporated by reference herein in their entirety.

What is claimed is:

1. An assay method for measuring the quantity of elemental gallium present in a test sample comprising a body tissue or a body fluid, the method comprising:

diluting said test sample in a matrix containing about 0.2% (volume/volume) of nitric acid, introducing said diluted test sample into an atomic absorption spectrometer having a Zeeman-effect background correction calculating capability, determining said test sample's absorption at a desired wavelength while subjecting said test sample to an atomization and a burning in said atomic absorption spectrometer, performing a Zeeman-effect background correction on said determined absorption for said test sample to give a corrected absorption for said test sample, and comparing said corrected absorption for said test sample with a standard curve.

2. The assay method according to claim 1, wherein said body tissue and said body fluid is from a human.

3. The assay method according to claim 1, wherein said desired wavelength is about 287 nanometers.

4. The assay method according to claim 1, wherein said desired wavelength is about 287.4 nanometers.

5. The assay method according to claim 1, wherein said atomization of said test sample occurs at a temperature of about 2400° C.

6. The assay method according to claim 1, wherein said burning of said test sample occurs at a temperature of about 2600° C.

* * * * *